United States Patent
Niino (10) Patent No.: US 11,284,780 B2
(45) Date of Patent: Mar. 29, 2022

(54) ENDOSCOPE DEVICE

(71) Applicant: OLYMPUS CORPORATION, Hachioji (JP)

(72) Inventor: Rieko Niino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 566 days.

(21) Appl. No.: 16/181,310

(22) Filed: Nov. 5, 2018

(65) Prior Publication Data
US 2019/0069765 A1 Mar. 7, 2019

Related U.S. Application Data

(63) Continuation of application No. PCT/JP2017/017268, filed on May 2, 2017.

(30) Foreign Application Priority Data

May 11, 2016 (JP) .............................. JP2016-095175

(51) Int. Cl.
*A61B 1/00* (2006.01)
*A61B 1/005* (2006.01)
(Continued)

(52) U.S. Cl.
CPC .......... *A61B 1/00142* (2013.01); *A61B 1/005* (2013.01); *A61B 1/0011* (2013.01);
(Continued)

(58) Field of Classification Search
CPC ... A61B 1/00142; A61B 1/0011; A61B 1/005; A61B 1/0055; A61M 25/0045; G02B 23/2476
(Continued)

(56) References Cited

U.S. PATENT DOCUMENTS 5,947,979 A * 9/1999 Ouchi .................... D07B 5/007
606/113
8,206,286 B2 * 6/2012 Sato ................... G02B 23/2476
600/139
(Continued)

FOREIGN PATENT DOCUMENTS

CN        1844534 A      10/2006
CN      102821668 A      12/2012
(Continued)

OTHER PUBLICATIONS

Chinese Office Action (and English translation thereof) dated May 25, 2020, issued in counterpart Chinese Application No. 201780026396.5.
(Continued)

*Primary Examiner* — Alexandra L Newton
(74) *Attorney, Agent, or Firm* — Holtz, Holtz & Volek PC (57) ABSTRACT

An endoscope device is provided, which includes: an insertion part inserted into an examination subject; an outer coat tube disposed at an outer circumferential portion of the insertion part; a fixing member at least a part of which is inserted into the outer coat tube, and the fixing member being in contact with an inner circumferential surface of the outer coat tube; a tight binding thread wound around the outer coat tube, the tight binding thread being made flat in a state in which at least a void is pressed to be flattened, and the tight binding thread being wound such that a longitudinal surface in a flat cross section of the tight binding thread is in contact with an outer circumferential surface of the outer coat tube; and a resin layer formed on the outer coat tube to cover the tight binding thread.

8 Claims, 3 Drawing Sheets

(51) Int. Cl.
*G02B 23/24* (2006.01)
*A61M 25/00* (2006.01)

(52) U.S. Cl.
CPC ....... *A61B 1/0055* (2013.01); *A61M 25/0045* (2013.01); *G02B 23/2476* (2013.01)

(58) Field of Classification Search
USPC .......................................................... 600/140
See application file for complete search history.

(56) References Cited

U.S. PATENT DOCUMENTS

| | | | |
|---|---|---|---|
| 9,188,773 | B2 | 11/2015 | Abe |
| 2006/0258911 | A1 | 11/2006 | Sato |
| 2013/0035549 | A1* | 2/2013 | Abe .................. G02B 23/2476 600/121 |

FOREIGN PATENT DOCUMENTS

| | | | | |
|---|---|---|---|---|
| JP | 55109503 | U | | 7/1980 |
| JP | H05277061 | A | | 10/1993 |
| JP | 2005021243 | A | * | 1/2005 ............ B32B 27/08 |
| JP | 2006340909 | A | | 12/2006 |
| JP | 2012213482 | A | | 11/2012 |

OTHER PUBLICATIONS

International Search Report (ISR) dated Jul. 18, 2017 issued in International Application No. PCT/JP2017/017268.
Written Opinion dated Jul. 18, 2017 issued in International Application No. PCT/JP2017/017268.
Chinese Office Action (and English translation thereof) dated May 25, 2020, issued in counterpart Chinese Application No. 201780026393.5.

* cited by examiner

ENDOSCOPE DEVICE

This application is a continuation application based on PCT Patent Application No. PCT/JP 2017/017268, filed May 2, 2017, claiming priority based on Japanese Patent Application No. 2016-095175, filed May 11, 2016, the contents of which are incorporated herein by reference.

BACKGROUND OF THE INVENTION

Field of the Invention

The present invention relates to an endoscope device.

Description of the Related Art

Conventionally, a variety of medical and industrial endoscope devices are known.

For example, medical endoscope devices are used for examinations, diagnosis, etc. to the digestive tract or the like. A medical endoscope device includes an insertion part inserted into a body cavity of a patient who is an examination subject, a manipulation part, a light source part, and a monitor.

An imaging device is disposed on a distal end portion of the insertion part. An image of the inside of a body cavity picked up by the imaging device is displayed on the monitor.

The insertion part has a long flexible tube part, and a bendable part that is bendable and is connected to a distal end portion of the flexible tube part. An operator rotates the insertion part and bends the bendable part via the manipulation part. Thereby, the operator can observe the inside of a body cavity, or insert a treatment tool into the endoscope device to perform various treatments.

For example, electrical wiring, a light guide, a treatment tool channel into which a treatment tool is inserted, etc. are inserted into the insertion part.

Industrial endoscope devices are used for inspection or the like of the inside of an examination subject such as an industrial plant, a jet engine, and so on. Like a medical endoscope device, an industrial endoscope device also includes a light source part, a monitor, and so on.

In these endoscope devices, outer circumferences of the flexible tube part and the bendable part of the insertion part are covered with an outer coat tube having flexibility.

Both ends of the outer coat tube of the insertion part need to be scaled in a liquid-tight way in order to protect the built-in elements inserted into the insertion part. For this reason, the outer coat tube is fixed to the insertion part by being wound a tight binding thread around the outer coat tube from outward.

For example, an endoscope device in which an outer circumference of a joint part between two flexible tubes (outer coat tubes) is tightened with a thread made of a synthetic or natural fiber and in which a skin layer formed of a synthetic resin material is formed on an outer side of the joint is disclosed in Japanese Unexamined Patent Application, First Publication No. H05-277061.

As a tight binding thread used for such the endoscope device, for example, a fiber single thread having a large diameter or a twisted thread disclosed in Japanese Unexamined Patent Application, First Publication No. 2006-340909 may be used.

SUMMARY OF THE INVENTION

The present invention adopts, for instance, a hollow yarn for a tight binding thread that is wound around an outer coat tube to fix the outer coat tube in an endoscope device. When the hollow yarn is wound to have a void in a central portion thereof, the void portion is pressed to have a flat cross section, and thus an increase in diameter of the endoscope device due to winding is small. The hollow fiber may be a filament having a tubular shape, but a plurality of strands are preferably braided together to form the hollow yarn because elasticity is then increased.

According to a first aspect of the present invention, an insertion part configured to be inserted into an examination subject; an outer coat tube disposed at an outer circumferential portion of the insertion part; a fixing member at least a part of which is inserted into the outer coat tube, the fixing member being in contact with an inner circumferential surface of the outer coat tube; a tight binding thread wound around the outer coat tube and configured to fix the outer coat tube to the fixing member, the tight binding thread being made flat in a state in which at least a void of a central portion of the tight binding thread in a radial direction is pressed to be flattened, and the tight binding thread being wound such that a longitudinal surface in a flat cross section of the tight binding thread is in contact with an outer circumferential surface of the outer coat tube; and a resin layer formed on the outer coat tube to cover the tight binding thread.

According to a second aspect of the present invention, in the endoscope device according to the first aspect of the present invention, the tight binding thread may be a tubular net-like body.

According to a third aspect of the present invention, in the endoscope device according to the second aspect of the present invention, the net-like body may be braided by a plurality of threads.

According to a fourth aspect of the present invention, in the endoscope device according to the first aspect of the present invention, the tight binding thread may include a fiber formed of at least one of an aramid resin, a polyarylate resin, and a polyester resin.

According to a fifth aspect of the present invention, in the endoscope device according to the first aspect of the present invention, in a state in which the tight binding thread is wound around the outer coat tube, a lengthwise width of a flattened shape in a cross section perpendicular to a winding direction may be no less than twice and no more than four times a lateral width of the flattened shape.

According to a sixth aspect of the present invention, in the endoscope device according to the first aspect of the present invention, the tight binding thread may be formed by winding a raw material thread whose thickness, which is a lateral width of a flattened shape, may be no less than 0.01 mm and no more than 0.3 mm when the raw material thread is sandwiched between surfaces in a straight-line state in which no tensile force is applied, and may be pressed with a force of 3.5 N.

DETAILED DESCRIPTION OF THE INVENTION

Hereinafter, an endoscope device according to an embodiment of the present invention will be described with reference to the attached drawings.

Figure 1:
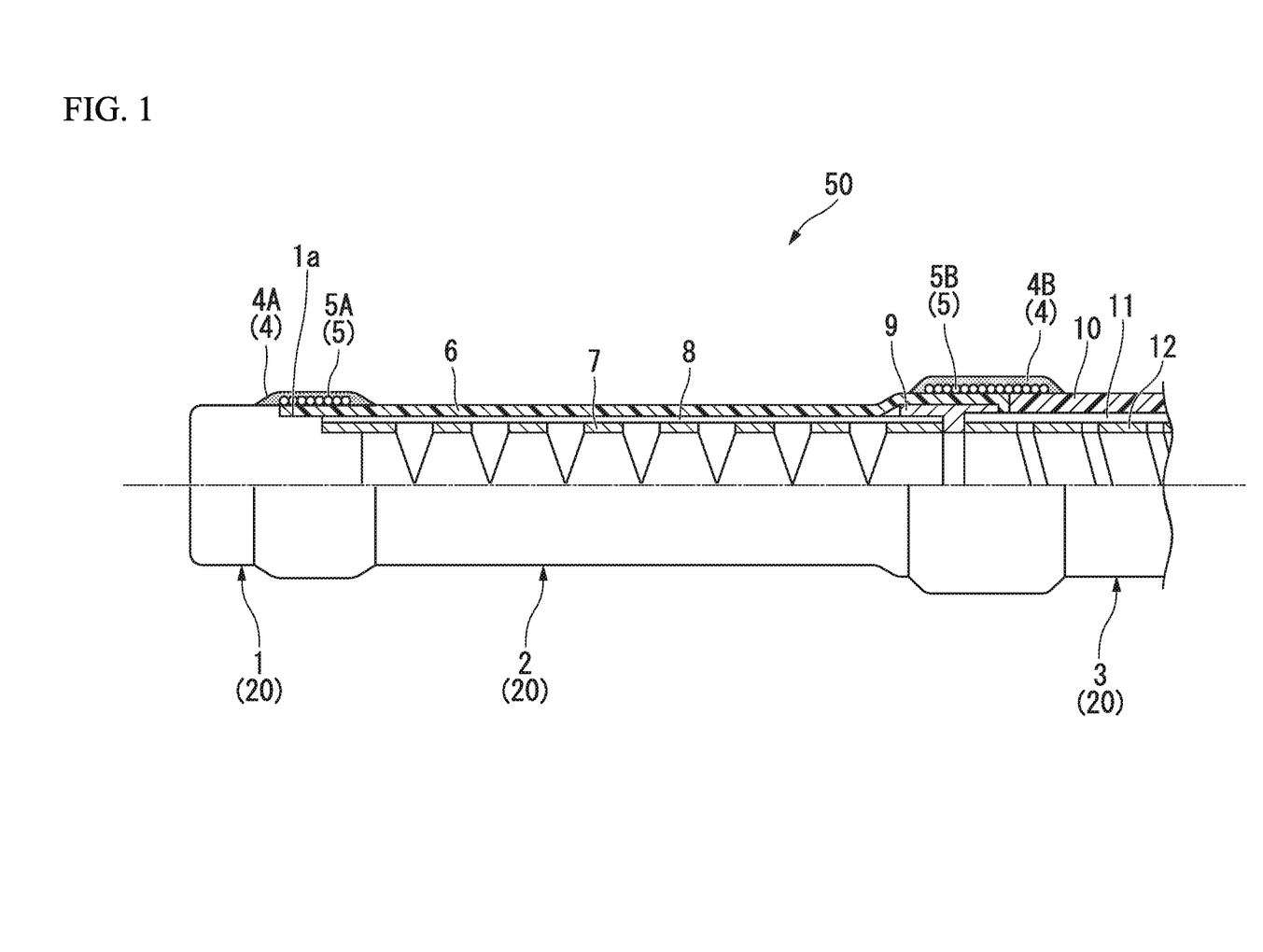
FIG. 1 is a schematic partial sectional view illustrating configurations of main portions of an endoscope device according to an embodiment of the present invention.

FIG. 1 is a schematic partial sectional view illustrating an example in which principal parts of an endoscope device according to an embodiment of the present invention are formed.

As illustrated in FIG. 1, an endoscope device 50 according to the present embodiment includes an insertion part 20 configured to be inserted into an examination subject. An outline of the insertion part 20 is a long columnar shape. Various built-in elements to be described below are housed in the insertion part 20. The insertion part 20 has flexibility.

A structure around a distal end of the insertion part 20 in an inserting direction is illustrated in FIG. 1. A manipulation part of the endoscope device 50 is coupled to an end portion (not shown) on the side opposite to the distal end portion of the insertion part 20.

Uses of the endoscope device 50 and types of examination subject are not limited. The endoscope device 50 may be for medical use in which the examination subject is a living body, or for industrial use in which the examination subject is not a living body.

A camera portion 1 in which an optical system (not shown), an imaging device, etc. are installed is disposed on an end of the insertion portion 20 on the distal end side (the left side in the figure).

A bendable part 2 and a flexible tube 3 are coupled close to a proximal end (at the shown right side) of the camera part 1 in this order.

The bendable part 2 is bent by manipulation of the manipulation part (not shown), so that a position and orientation of the distal end portion of the insertion part 20 is capable of being changed.

The bendable part 2 includes a plurality of joint rings 7 that are coupled to be tiltable with respect to each other in order to perform a bending operation, a metal net-like tube 8 that covers outer surfaces of the plurality of joint rings 7, and an outer coat tube 6 that covers an outer side of the metal net-like tube 8 and is disposed on an outer circumferential portion of the insertion part 20.

An insertion space, which passes through the bendable part 2 in a longitudinal direction, is formed inside the joint rings 7. Although not particularly shown, built-in elements including, for instance, electrical wiring (not shown) that is connected to the camera part 1, a light guide that guides illumination light, a manipulating wire, and a treatment tool channel are inserted into the insertion space in a longitudinal direction.

The outer coat tube 6 is formed of a tubular member such as a rubber tube which has flexibility. When the endoscope device 50 is for medical use, a material resistant to sterilization treatment is used for the outer coat tube 6.

An inner circumferential surface of a distal end portion of the outer coat tube 6 is fitted onto a fixing part 1a which is provided on an outer circumferential portion of the camera part 1. The inner circumferential surface of the outer coat tube 6 fitted onto the fixing part 1a abuts the fixing part 1a in a state in which the outer coat tube 6 is tightened from an outer circumferential side by a tight binding thread 5A to be described below. At least a part of the fixing part 1a is inserted into the outer coat tube 6 and the fixing part 1a constitutes a fixing member which abuts on the inner circumferential surface of the outer coat tube 6.

The tight binding thread 5A is covered with a resin layer 4A that is formed on outer circumferential surfaces of the fixing part 1a and the outer coat tube 6.

For example, the resin layer 4A is formed by applying an adhesive onto the fixing part 1a and the outer coat tube 6 to cover the tight binding thread 5A and by curing the adhesive.

In the present embodiment, the resin layer 4A radially protrudes outward from the outer coat tube 6 at a middle portion of the bendable part 2. To reduce an outer diameter of the insertion part 20, an outer diameter of the resin layer 4A is better to reduce as small as possible within a range within which the tight binding thread 5A is possible to protect.

The resin layer 4A may be formed of a suitable resin material having necessary durability in an operating environment of the insertion part 20. Examples of the material for the adhesive of which the resin layer 4A is formed include an epoxy adhesive, an acrylic adhesive, a urethane-based adhesive, a hot-melt adhesive, and so on.

The flexible tube 3 includes a spiral tube 12, a metal net-like tube 11, and an outer coat tube 10. The spiral tube 12 is formed by winding a metal band. The metal net-like tube 11 covers an outer surface of the spiral tube 12. The outer coat tube 10 covers an outer surface of the metal net-like tube 11 and is disposed at the outer circumferential portion of the insertion part 20.

An insertion space passing through the flexible tube 3 in a longitudinal direction thereof is formed inside the spiral tube 12. The built-in elements as described above, which extend from the bendable part 2 toward a proximal end are inserted into the insertion space in the longitudinal direction. However, a manipulating wire (not shown) is inserted into the spiral tube 12 along with a coil sheath (not shown) in a state in which the manipulating wire is inserted into the coil sheath.

The outer coat tube 10 is formed of, for instance, a tubular member such as a resin tube which has flexibility. When the endoscope device 50 is for medical use, a material resisting sterilization like the outer coat tube 6 is used for the outer coat tube 10.

A proximal end portion of the bendable part 2 and a distal end portion of the flexible tube 3 are coupled via a connecting tube (a fixing member) 9. A joint ring 7 located on the proximal side is internally fitted to a distal end side of the connecting pipe 9 while sandwiching the metallic mesh tube 8 therebetween. A distal end portion of the spiral tube 12 is internally fitted close to a proximal end of the connecting tube 9 while sandwiching the metal net-like tube 11 therebetween.

In the present embodiment, an inner circumferential surface of a proximal end portion of the outer coat tube 6 is fitted onto the connecting tube 9 and the metal net-like tube 11 exposed from the proximal end of the connecting tube 9.

A distal end of the outer coat tube 10 abuts a proximal end of the outer coat tube 6.

The outer coat tubes 6 and 10 close to the connecting tube 9 are tightened with a tight binding thread 5B to be described below. The outer coat tube 6 is tightened from an outer circumferential side with the tight binding thread 5B, thereby the inner circumferential surface of the outer coat tube 6 is in contact with the connecting tube 9 and the metal net-like tube 11. At least a part of the metal net-like tube 11 and at least a part of the metal net-like tube 11 are inserted into the outer coat tube 6 and the metal net-like tube 11 constitute a fixing member which is in contact with the inner circumferential surface of the outer coat tube 6.

The outer coat tube 6 is tightened from an outer circumferential side with the tight binding thread 5B, thereby an inner circumferential surface of the outer coat tube 10 is in contact with the metal net-like tube 11. At least a part of the metal net-like tube 11 is inserted into the outer coat tube 6 and the metal net-like tube 11 constitutes a fixing member which is in contact with the inner circumferential surface of the outer coat tube 10.

The tight binding thread 5B is covered with a resin layer 4B that is formed on outer circumferential surfaces of the outer coat tubes 6 and 10.

For example, the resin layer 4B is formed by applying an adhesive onto the outer coat tubes 6 and 10 to cover the tight binding thread 5B and by curing the adhesive.

In the present embodiment, the resin layer 4B radially protrudes outside the outer coat tube 6 at a middle portion of the bendable part 2 and outside the outer coat tube 10 at a middle portion of the flexible tube 3. To reduce the outer diameter of the insertion part 20, an outer diameter of the resin layer 4B is better to reduce as small as possible within a range within which the tight binding thread 5B is possible to protect.

The resin layer 4B may be formed of a suitable resin material having necessary durability in the operating environment of the insertion part 20. The resin layer 4B may be formed of the same adhesive as the resin layer 4A.

The tight binding threads 5A and 5B may be the same members or different members.

Hereinafter, a case in which the tight binding threads 5A and 5B are the same members will be described as an example. When there is no need to distinguish places to be tightened, the tight binding threads 5A and 5B may be collectively referred to as a tight binding thread 5. Likewise, when there is no need to particularly distinguish the resin layers 4A and 4B, the resin layers 4A and 4B may be collectively referred to as a resin layer 4.

Figure 2:
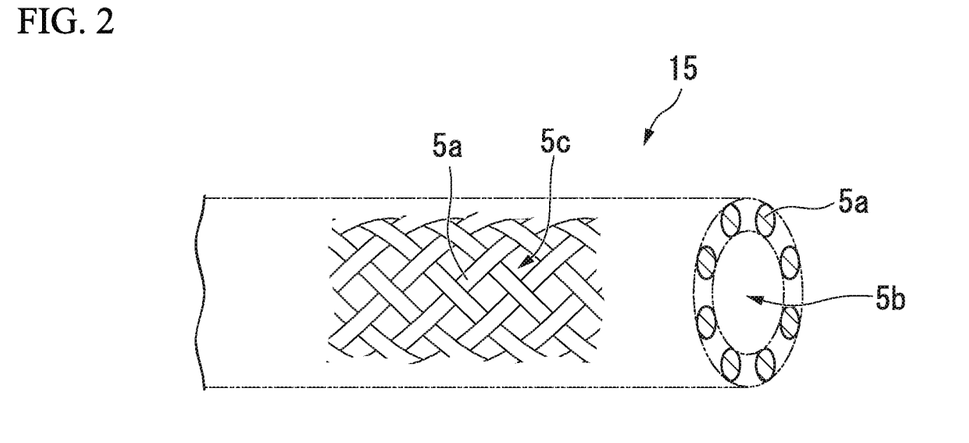
FIG. 2 is a schematic perspective view illustrating configurations of main portions of a tight binding thread used for the endoscope device according to the embodiment of the present invention.

FIG. 2 is a schematic perspective view illustrating an example of the configuration of the tight binding thread used for the endoscope device according to the embodiment of the present invention is formed.

The tight binding thread 5 is constituted of a raw material thread, which has a void formed in a central portion of the raw material thread in a radial direction (hereinafter referred to simply as a central portion), is wound around the outer circumferential surface of the outer coat tube 6 or the outer coat tube 10. The tight binding thread 5 is configured such that the void of the central portion in the raw material thread is pressed to be flattened and has a flat sectional shape.

The raw material thread of the tight binding thread 5 is formed of a material in which the void of the central portion is at least pressed when the raw material thread is wound around the outer circumferential surface of the outer coat tube 6 or the outer coat tube 10.

For example, the raw material thread 15 schematically drawn in FIG. 2 is a tubular net-like body formed by braiding a plurality of yarns 5a. The yarns 5a may be filaments or twisted yarns.

A hollow portion 5b, which is a void passing through in an axial direction, is formed in the central portion of the raw material thread 15 on an inner side of the yarns 5a located at an inner circumferential portion of the raw material thread 15.

A braid method for the raw material thread 15 is not limited as long as the hollow portion 5b is formed, and the raw material thread 15 is wrapped around the outer coat tube 6 or the outer coat tube 10 so that the hollow portion 5b can be pressed and deformed to be flat. The braid method for the raw material thread 15 that is schematically illustrated in FIG. 2 is an example.

As illustrated in FIG. 2, the raw material thread 15 may be manufactured by a braid method by which voids 5c communicating with the hollow portion 5b from the vicinity of an outer circumference of the raw material thread 15 are formed between the yarns 5a.

Sizes of the voids 5c may be larger or smaller than outer diameters of the yarns 5a. The raw material thread 15 may be manufactured by a dense braid method by which the voids 5c are substantially blocked as long as the hollow portion 5b is capable of being pressed to be flattened.

Since FIG. 2 is a schematic view, the raw material thread 15 is drawn in a cylindrical shape. However, the raw material thread 15 may be formed in a tubular shape, such as an elliptical tubular shape, that is different from a cylindrical shape as long as the hollow portion 5b is continuously formed in the longitudinal direction of the raw material thread 15. A thickness (an outer diameter) of the raw material thread 15 or a cross-sectional shape of the hollow portion 5b may vary in the longitudinal direction as long as the hollow portion 5b is continuously formed in the longitudinal direction of the raw material thread 15.

The number of yarns 5a in the raw material thread 15 is not limited if the hollow portion 5b is formable. The number of yarns 5a may be more than or equal to eight. The number of yarns 5a can be appropriately determined in consideration of a strength of the raw material thread 15 and a flattened shape after the raw material thread 15 is wound along with thicknesses of the yarns 5a.

An operation of the raw material thread 15 in which the hollow portion 5b is formed will be described.

Figure 3A:
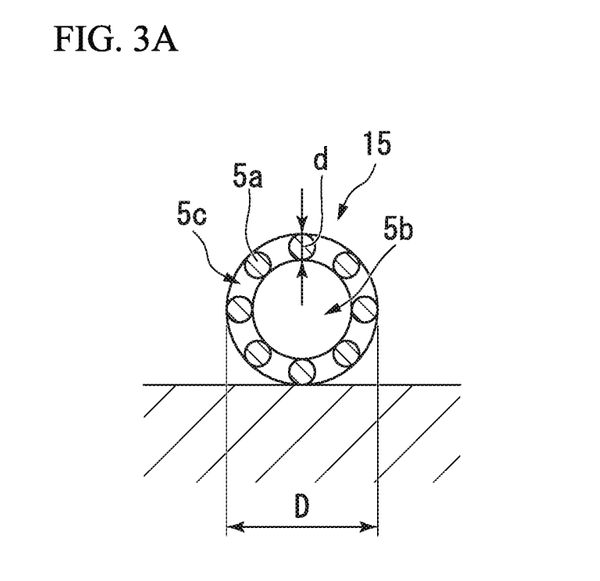
FIG. 3A is a schematic view illustrating characteristics of a raw material thread of the tight binding thread used for the endoscope device according to the embodiment of the present invention.
Figure 3B:
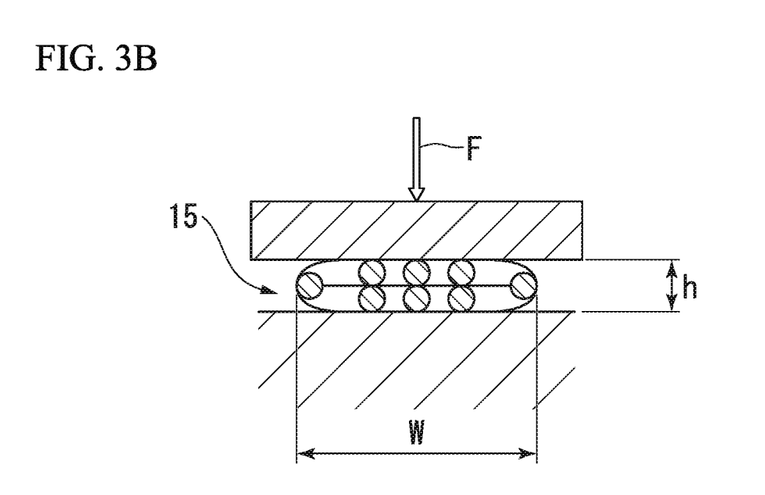
FIG. 3B is a schematic view illustrating characteristics of a raw material thread of the tight binding thread used for the endoscope device according to the embodiment of the present invention.

FIG. 3A and FIG. 3B are schematic views illustrating characteristics of the raw material thread of the tight binding thread used for the endoscope device according to the embodiment of the present invention.

As illustrated in FIG. 3A, the raw material thread 15 has, for instance, an approximately cylindrical shape in an unloaded state. Since the hollow portion 5b is formed in the raw material thread 15, an outer diameter D of the raw material thread 15 is larger than twice as an outer diameter d of the yarn 5a.

As illustrated in FIG. 3B, when an external force F is applied to the raw material thread 15 in a radial direction, the hollow portion 5b is pressed and deformed to be flat. Hereinafter, a flattened shape in a cross section perpendicular to the longitudinal direction of the raw material thread 15 is expressed in terms of a width (a lengthwise width) W in a direction perpendicular to a pressing direction, and a width (a lateral width, a thickness) h of the pressing direction.

The lengthwise width W and the lateral width h vary according to the thickness of the yarn 5a, the number of yarns 5a, the size of the hollow portion 5b, the material of the yarns 5a, the braid method for the raw material thread 15, the external force at the time of flattening, or the like.

To compare flattening characteristics of the raw material thread 15, there is a need to compare when keeping flattening conditions constant. In the present embodiment, as illustrated in FIG. 3B, the flattening characteristics of the raw material thread 15 are restricted by the lengthwise width W and the lateral width h of the flattened shape when the raw material thread 15 is sandwiched between surfaces in a straight-line state in which no tensile force is applied, and is pressed with a force of F=3.5 (N).

Flat plates or the like, which are made of, for instance, a ceramic or a metal and have good slidability, are used as the surfaces that flatten the raw material thread 15. For example, a thickness gauge having a flat probe may be used as measuring means for the lateral width h.

In the flattened shape of the raw material thread 15 pressed with the force F, the lateral width h is preferably no less than 0.01 mm and no more than 0.3 mm.

The lengthwise width W is preferably no less than twice and no more than four times the lateral width h.

When compressive deformation of the yarns 5a itself is negligible, the lateral width h at least satisfies h=2d.

When an inner circumference of the hollow portion 5b having an inner diameter of (D−2d) is pressed with a circumferential length maintained, the lengthwise width W satisfies W=π(D−2d)/2.

However, since the deformation of the raw material thread 15 is actually complicated, a suitable thickness of the raw material thread or a size of the hollow portion 5b is preferably determined, for instance, by performing a flattening experiment with a prototype of the raw material thread 15 which is obtained by suitably changing the thickness, the number, the braid method, etc. of the filaments of the raw material thread 15.

Since the hollow portion 5b is pressed and deformed to be flat when the raw material thread 15 is wound around the outer coat tubes 6 and 10, a height of the raw material thread 15 from the outer coat tubes 6 and 10 in a wound state is reliably made lower than an outer diameter D of the raw material thread 15 in an unloaded state.

A material of the yarn 5a is not limited if a necessary tightening strength is obtained. The yarn 5a may be formed of synthetic fibers or natural fibers. The yarn 5a may be formed of the same fibers, or be a blended yarn. The yarn 5a may be a blended yarn of a synthetic fiber and a natural fiber.

The plurality of yarns 5a in the raw material thread 15 may be all formed of the same material, or include yarns whose materials are different.

The yarn 5a may be configured to include a fiber formed of at least one of an aramid resin, a polyarylate resin, and a polyester resin. A tensile strength of the yarn 5a is improved by including fibers formed of any of these resins.

Examples of an aramid fiber include Technora (registered trademark) (trade name, available from Teijin), which is a para-aramid fiber.

Examples of the polyarylate fiber include Vectran (registered trademark) (trade name, available from Kuraray).

Figure 4:
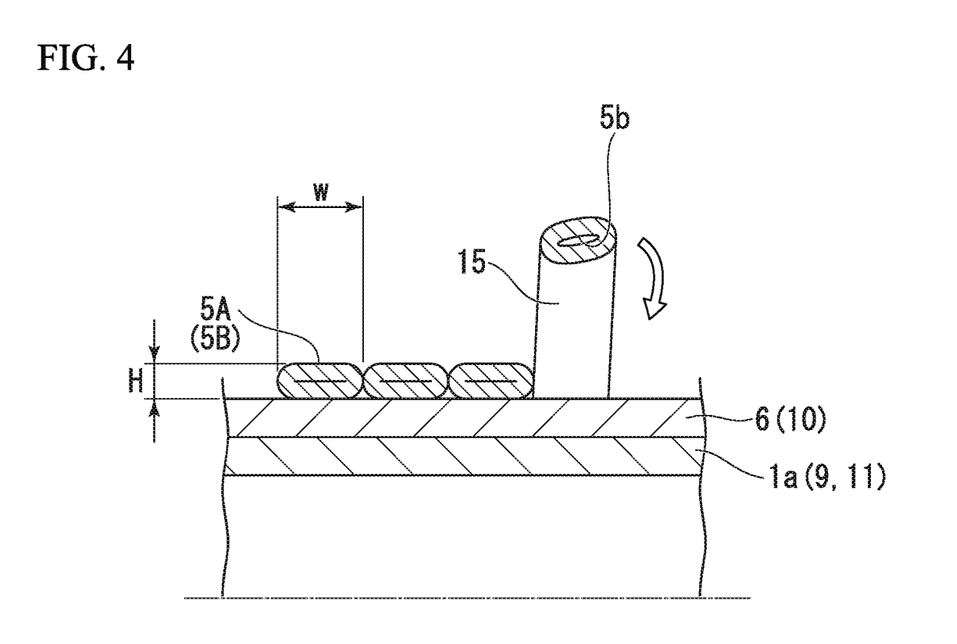
FIG. 4 is a schematic view illustrating a process of manufacturing the endoscope device according to the embodiment of the present invention.

A method of manufacturing the endoscope device 50 will be described on the basis of a fixing method for the outer coat tubes 6 and 10 using the tight binding thread 5.

FIG. 4 is a schematic view illustrating a process of manufacturing the endoscope device according to the embodiment of the present invention.

Since the outer coat tubes 6 and 10 are similarly fixed, a case in which the outer coat tube 6 is fixed to the fixing part 1a will be described below by way of example.

As illustrated in FIG. 4, first, the outer coat tube 6 is fitted onto the fixing part 1a, which is a fixing member. Afterward, the raw material thread 15 is wound around the outer circumferential portion of the outer coat tube 6.

In this case, the raw material thread 15 is pressed toward the center of the outer coat tube 6 on the outer circumferential surface of the outer coat tube 6, and thus the hollow portion 5b is pressed and deformed to be flat, and the raw material thread 15 as the tight binding thread 5A comes into close contact with the outer coat tube 6 as the tight binding thread 5A.

The tight binding thread 5A has a flattened shape in which, in a cross section perpendicular to a winding direction of the tight binding thread 5A (to a longitudinal direction of the raw material thread 15), for instance, a lengthwise width×a lateral width is w×H.

The lateral width H may be no less than 0.01 mm and no more than 0.3 mm.

The lengthwise width w is preferably no less than twice and no more than four times the lateral width H.

In a winding operation of the raw material thread 15, completely the same conditions as measurement conditions of the aforementioned flattening characteristics of the raw material thread 15 are not satisfied, and furthermore operation variation also occurs. For this reason, the lengthwise width w (the lateral width H) may not correspond to the lengthwise width W (the lateral width h), and is nearly equal to the lengthwise width W (the lateral width h).

When the raw material thread 15 is wound within a predetermined range and a wound portion of the tight binding thread 5A which has a predetermined width is formed, a terminal portion of the raw material thread 15 is caused to pass through the wound portion, and then is cut.

Thus, the outer circumferential surface of the outer coat tube 6 is tightened with the tight binding thread 5A, and the inner circumferential surface of the outer coat tube 6 is pressed against the fixing part 1a. In this state, the outer coat tube 6 is fixed to the fixing part 1a.

Since the tight binding thread 5A is closely wound within a constant range of the outer coat tube 6 in a longitudinal direction, the outer coat tube 6 is constricted toward the center thereof within a cylindrical range within which the tight binding thread 5A is wound.

Since the outer coat tube 6 is elastically deformed depending on a tightening force, and comes into close contact with the fixing part 1a, the fixing part 1a and the outer coat tube 6 are sealed in a liquid-tight way.

Similarly, tightening of the tight binding thread 5B is performed. Afterward, an adhesive is applied onto each of the tight binding threads 5A and 5B, and is cured, so that the resin layers 4A and 4B are formed.

Thus, the fixture of the outer coat tubes 6 and 10 at the insertion part 20 is terminated.

According to the endoscope device 50, the inside of the insertion part 20 is kept liquid-tight by the outer coat tubes 6 and 10 fixed by the tight binding thread 5.

The tight binding thread 5 comes into close contact with the outer coat tubes 6 and 10 in the state in which the raw material thread 15 in which the hollow portion 5b is formed is pressed to be flat.

As illustrated in FIG. 3B, when the raw material thread 15 is pressed to be flat, the yarns 5a are layered in nearly two layers, and the neighboring yarns 5a are adjacent to each other within the lengthwise width having a flattened shape.

In contrast, for example, the case of a comparative example of a twisted yarn caused by the same number of yarns 5a with no hollow portion 5b is considered. Since the twisted yarn of the comparative example has the same number of yarns 5a, a tensile strength is the same as the tight binding thread 5.

However, the twisted yarn of the comparative example has an approximately circular cross-sectional shape before being wound. Even when the twisted yarn of the comparative example is wound and somewhat pressed, the yarns 5a themselves are merely deformed and pressed. For this reason, a lengthwise width having a flattened shape of the twisted yarn of the comparative example slightly exceeds about 1 times a lateral width, and does not reach two or more times the lateral width.

For this reason, although the tight binding thread 5 in the present embodiment has the same strength as the twisted yarn of the comparative example, a thickness of the tight binding thread 5 that has been tightened is definitely made thinner, compared to the twisted yarn of the comparative example, so that the outer diameter of the insertion part 20 is capable of being made smaller.

Furthermore, according to the tight binding thread 5, since the tight binding thread 5 is wound in a flat state, the number of turns when the tight binding thread 5 is wound within a constant width is made smaller, compared to the twisted yarn of the comparative example. For this reason, the winding operation is rapidly performed.

Such an action is possible to be obtained even when a band-like yarn having the same shape as the tight binding thread 5 is wound. However, in the case of the band-like yarn that has been previously flattened, a tightening force varies when the band-like yarn is wound in a twisted state. For this reason, the band-like yarn needs to be wound such that it is not twisted. However, since a yarn that can be used for tightening has a width of about 1 mm even if it is lengthwise, it is very difficult to wind the yarn such that the yarn is not twisted, so that winding operation efficiency is lowered, and there is a need to rewind the yarn when the yarn is twisted.

In the case of the tight binding thread 5, since the tight binding thread 5 is pressed against the outer coat tube 6 or the like during the winding operation and is thereby flattened, the tight binding thread 5 is capable of being easily and rapidly wound without paying special attention.

In this way, the outer coat tubes 6 and 10 are fixed by the tight binding thread 5, so that the outer diameter of the insertion part 20 is capable of being made smaller, and the endoscope device 50 is capable of being easily manufactured.

In the description of the above embodiment, the tight binding thread 5 made up of the tubular net-like body in which the yarns 5a are braided, and thereby the hollow portion 5b is formed has been described by way of example.

However, the tubular net-like body used for the tight binding thread may be made up of a tubular net-like body into which yarns are not braided. For example, the tubular net-like body used for the tight binding thread may be a tubular net-like body formed in such a way that numerous micropores pass through an outer surface of a tubular hollow fiber, in a central portion of which a hollow portion is formed.

In the description of the above embodiment, the tight binding thread 5 made up of the tubular net-like body in which the hollow portion 5b is formed has been described by way of example.

However, the tight binding thread may be formed of a tubular filament, in a central portion of which a hollow portion is formed, if the tight binding thread is capable of being deformed to be flat.

EXAMPLES

Hereinafter, Examples 1 to 4 of the above embodiment will be described along with Comparative Examples 1 to 4.

In Table 1 below, constitutions and evaluation results of tight binding threads of Examples 1 to 4 and Comparative Examples 1 to 4 are shown.

TABLE 1

| | Constitution of tight binding thread | | | | | | Evaluation | | | | |
|---|---|---|---|---|---|---|---|---|---|---|---|
| | Type | Hollow portion | Material | Thickness of filament (dtex) | Number of filament | Flat Thickness (mm) | Flat portion (Lengthwise width/lateral width) | Liquid-Tightness | Outer diameter increment (mm) | Determination | Total |
| Example 1 | Braided yarn | Presence | High-strength aramid fiber | 61 | 8 | 0.12 | 2.9 | ○ | +0.25 | ○ | ○ |
| Example 2 | Braided yarn | Presence | High-strength polyarylate fiber | 56 | 8 | 0.12 | 2.8 | ○ | +0.25 | ○ | ○ |
| Example 3 | Braided yarn | Presence | High-strength aramid fiber | 28 | 16 | 0.12 | 2.9 | ○ | +0.25 | ○ | ○ |
| Example 4 | Braided yarn | Presence | High-strength polyarylate fiber | 28 | 16 | 0.12 | 2.8 | ○ | +0.25 | ○ | ○ |
| Comparative Example 1 | Filament | Absence | PET yarn | — | 1 | 0.2 | 1.2 | ○ | +0.4 | X | X |
| Comparative Example 2 | Braided yarn | Absence | High-strength aramid fiber | 61 | 4 | 0.09 | 1.8 | X | +0.2 | ○ | X |
| Comparative Example 3 | Braided yarn | Absence | High-strength aramid fiber | 61 | 8 | 0.16 | 1.8 | ○ | +0.35 | X | X |
| Comparative Example 4 | Braided yarn | Absence | High-strength polyarylate fiber | 56 | 8 | 0.16 | 1.8 | ○ | +0.35 | X | X |

Example 1

A raw material thread 15 used as a tight binding thread 5 of Example 1 was formed by braiding eight Technoras (registered trademark) (trade name, available from Teijin), which acted as yarns 5a, were high-strength aramid fibers, and had a thickness of 61 dtex, into a tubular net-like body.

A lateral width h ("flat thickness" in Table 1) having a flattened shape when the raw material thread 15 of the example 1 was pressed with a force of F=3.5 (N) as described above was 0.12 mm.

As means for measuring the lateral width h, ABS Digimatic (registered trademark) Thickness Gauge ID-C112BS (Code No. 547-401) (trade name, available from Mitutoyo) was used.

The endoscope device 50 having the aforementioned constitution was manufactured using the raw material thread 15 of the example 1. Outer diameters of the fixing part 1a, the connecting tube 9, and the metal net-like tube 11 were 5.5 mm, 5.8 mm, and 5.6 mm, respectively. Outer diameters of the outer coat tubes 6 and 10 fitted onto them were 5.7 mm and 5.9 mm, respectively. The outer diameters of the outer coat tubes 6 and 10 were measured by the ABS Digimatic (registered trademark) Thickness Gauge ID-C112BS (Code No. 547-401) (trade name, available from Mitutoyo).

SUS304 (JIS) was used for materials of the fixing part 1a and the connecting tube 9. A fluororubber and a urethane resin were used for materials of the outer coat tubes 6 and 10, respectively.

The raw material thread 15 was wound around the fixing part 1a by four to seven turns, and thereby a tight binding thread 5A was formed.

The raw material thread 15 was wound around the connecting tube 9 and the metal net-like tube 11 by six to nine turns, and thereby a tight binding thread 5B was formed.

In the state in which the tight binding threads 5A and 5B were formed, a lengthwise width w and a lateral width H for a flattened shape in a wrapped state were measured. The column "Flat portion (Lengthwise width/Lateral width)" of Table 1 indicates a magnitude of w/H. The value of w/H given in Table 1 is an average value of the tight binding threads 5A and 5B.

Further, outer diameters of regions in which the tight binding threads 5A and 5B were wound were similar to those of the outer coat tubes 6 and 10, and were measured using the ABS Digimatic (registered trademark) Thickness Gauge ID-C112BS (Code No. 547-401) (trade name, available from Mitutoyo).

A maximum value of increments of the outer diameters of the regions in which the tight binding threads 5A and 5B were wound with respect to the outer diameters of the outer coat tubes 6 and 10 before tightening is given in the column "Outer diameter increment" of Table 1. In Example 1, the increment of outer diameter was +0.25 mm.

After the tight binding threads 5A and 5B were formed, an epoxy adhesive was applied and cured, so that resin layers 4A and 4B were formed.

Examples 2 to 4

Example 2 was formed by replacing the materials of the yarns 5a in Example 1 with eight Vectrans (registered trademark) (trade name, available from Kuraray) that were high-strength polyarylate fibers and had a thickness of 56 dtex.

Example 3 was formed by replacing the materials of the yarns 5a in Example 1 with 16 Technoras (registered trademark) (trade name, available from Teijin), which were high-strength aramid fibers and had a thickness of 28 dtex.

Example 4 was formed by replacing the materials of the yarns 5a in Example 1 with 16 Vectrans (registered trademark) (trade name, available from Kuraray) that were high-strength polyarylate fibers and had a thickness of 28 dtex.

As shown in Table 1, all lateral widths h of flattened shapes of raw material threads 15 of Examples 2 to 4 were 0.12 mm.

The raw material threads 15 of Examples 2 to 4 were wound by the same number of turns as the raw material thread 15 of Example 1. Flattening characteristics of Examples 2 to 4 were substantially similar to one another as could be seen from the fact that the lateral widths h were equal to one another, and thus all lengths of winding regions (hereinafter referred to as tightening widths) in a longitudinal direction of the insertion part 20 were substantially similar to one another.

As shown in Table 1, all the outer diameter increments caused by the tight binding threads 5 of Examples 2 to 4 were +0.25 mm.

Comparative Example 1

A raw material thread used as a tight binding thread of Comparative Example 1 was formed of one filament that had an outer diameter of 0.2 mm and was formed of a polyethylene terephthalate (PET) resin.

In the raw material thread of Comparative Example 1, even if a flattened shape was measured like the examples, a lateral width h thereof was 0.2 mm, which was the same as an outer diameter thereof.

The raw material thread of Comparative Example 1 was wound like Example 1, except that the number of turns was adjusted such that a tightening width was the same as that in Example 1.

As shown in Table 1, an outer diameter increment caused by the tight binding thread of Comparative Example 1 was +0.4 mm.

Comparative Examples 2 to 4

In Comparative Example 2, a braided yarn that was braided using four yarns 5a that were the same as in Example 1 was used. When the number of yarns 5a was four, it was impossible to form a tubular net-like body in which a hollow portion 5b was formed in an unloaded state.

As shown in Table 1, a lateral width h of the raw material thread of Comparative Example 2 was 0.09 mm.

In Comparative Example 3, a braided yarn that was braided using eight yarns 5a that were the same as in Example 1 was used. However, the braided yarn of Comparative Example 3 was braided by a braid method by which a hollow portion was not formed in a central portion thereof like Comparative Example 3.

A lateral width h of the raw material thread of Comparative Example 3 was 0.16 mm.

In Comparative Example 4, a braided yarn that was braided using eight yarns 5a that were the same as in Example 2 was used. However, the braided yarn of Comparative Example 4 was braided by a braid method by which a hollow portion was not formed in a central portion thereof like Comparative Example 3.

A lateral width h of the raw material thread of Comparative Example 4 was 0.16 mm.

Each of the raw material threads of Comparative Examples 2 to 4 was wound like Example 1, except that the number of turns was adjusted such that a tightening width became similar to that in Example 1.

As shown in Table 1, outer diameter increments caused by the tight binding threads of Comparative Examples 2 to 4 were +0.2 mm, +0.35 mm, and +0.35 mm.

[Evaluation]

In the evaluation of the examples and the comparative examples, evaluation of liquid-tightness was performed in addition to the measurement of the lengthwise width/lateral width of the tight binding thread and the outer diameter increment thereof.

The outer diameter increment caused by the tight binding thread represented an increment of the outer diameter of the insertion part when a resin layer having a constant layer thickness was formed on the tight binding thread. The outer diameter increment caused by the tight binding thread was determined to be good ("○" in Table 1) when it was no more than 0.3 mm, and to be no good ("x" in Table 1) when it exceeded 0.3 mm.

The evaluation of liquid-tightness was performed by sterilizing each endoscope device in which each tight binding thread was used 600 times with a vapor sterilizing apparatus in which vapor of 135° C. was used, feeding air of 0.05 MPa into the insertion part for three minutes, and checking whether or not air leakage occurred at the insertion part.

The liquid-tightness was determined to be good ("○" in Table 1) when air leakage did not occur, and to be no good ("x" in Table 1) when air leakage occurred.

[Evaluation Results]

As shown in Table 1, it can be especially seen that the tight binding threads of Examples 1 to 4 have the lengthwise width w/lateral width H of 2.8 to 2.9, and are flattened. Thus, it is found that the hollow portions of the raw material threads are pressed.

In contrast, it is found that Comparative Examples 1 to 4 have the lengthwise width w/lateral width H of 1.2 to 1.8, and are slightly flattened compared to Examples 1 to 4. This is because no hollow portions are formed in the central portions of all the raw material threads of Comparative Examples 1 to 4.

With respect to the liquid-tightness of the endoscope device manufactured by each tight binding thread, Examples 1 to 4 and Comparative Examples 1, 3 and 4 were good, whereas Comparative Example 2 was not good. This is thought to be because the tight binding thread cannot be tightly wound, and thus the tightening is insufficient.

With respect to the outer diameter increment caused by the tight binding thread, Examples 1 to 4 and Comparative Example 2 were good, whereas Comparative Examples 1, 3 and 4 were not good.

Even in the case of Comparative Examples 1, 3 and 4, if the thickness of the raw material thread is further reduced, the outer diameter increment is reduced, for instance, like Comparative Example 2. However, to reduce the thicknesses of Comparative Examples 1, 3 and 4, the thickness of the filament is reduced, but the number of filaments needs to be reduced. In any case, since the tensile strength is remarkably reduced, the liquid-tightness may be deteriorated like Comparative Example 2, or a durability strength of the tight binding thread may be deficient. In comparison with Examples 1 and 2 that are configured with the same number by the same filament, at least Comparative Examples 3 and 4 are definitely reduced in strength.

Therefore, the total evaluation is determined to be good ("○" in Table 1) when both the liquid-tightness and the outer diameter increment are good, and to be no good ("x" in Table 1) when at least one of the liquid-tightness or the outer diameter increment is not good.

According to the total evaluation, Examples 1 to 4 were good, and Comparative Examples 1 to 4 were not good.

While the preferred embodiment and examples of the present invention have been described, the present invention is not limited to these embodiment and examples. Additions, omissions, substitutions, and other modifications of the constitution are possible without departing from the spirit of the present invention.

In addition, the present invention is not limited by the aforementioned description, but is only limited by the appended claims.

What is claimed is:

1. An endoscope device, comprising:
   an insertion part insertable into an examination subject;
   an outer coat tube disposed at an outer circumferential portion of the insertion part;
   a fixing member at least a part of which is inserted into the outer coat tube, the fixing member being in contact with an inner circumferential surface of the outer coat tube;
   a tight binding thread wound around the outer coat tube and configured to fix the outer coat tube to the fixing member, the tight binding thread being made flat in a state in which at least a void of a central portion of the tight binding thread in a radial direction is pressed to be fully flattened, and the tight binding thread being wound such that a longitudinal surface in a flat cross section of the tight binding thread is in contact with an outer circumferential surface of the outer coat tube; and
   a resin layer formed on the outer coat tube to cover the tight binding thread,
   wherein the tight binding thread is a tubular net-like body.

2. The endoscope device according to claim 1, wherein the net-like body is braided by a plurality of threads.

3. The endoscope device according to claim 1, wherein the tight binding thread includes a fiber formed of at least one resin selected from an aramid resin, a polyarylate resin, and a polyester resin.

4. The endoscope device according to claim 1, wherein, in a state in which the tight binding thread is wound around the outer coat tube, a lengthwise width of a flattened shape in a cross section perpendicular to a winding direction is no less than twice and no more than four times a lateral width of the flattened shape.

5. The endoscope device according to claim 1, wherein the tight binding thread is formed by winding a raw material thread whose thickness, which is a lateral width of a flattened shape, is no less than 0.01 mm and no more than 0.3 mm when the raw material thread is sandwiched between surfaces and is pressed with a force of 3.5 N in a straight-line state in which no tensile force is applied.

6. An endoscope device, comprising:
   an insertion part insertable into an examination subject;
   an outer coat tube disposed at an outer circumferential portion of the insertion part;
   a fixing member at least a part of which is inserted into the outer coat tube, the fixing member being in contact with an inner circumferential surface of the outer coat tube;
   a tight binding thread wound around the outer coat tube and configured to fix the outer coat tube to the fixing member, the tight binding thread being made flat in a state in which at least a void of a central portion of the tight binding thread in a radial direction is pressed to be fully flattened, and the tight binding thread being wound such that a longitudinal surface in a flat cross section of the tight binding thread is in contact with an outer circumferential surface of the outer coat tube; and
   a resin layer formed on the outer coat tube to cover the tight binding thread, wherein, in a state in which the tight binding thread is wound around the outer coat tube, a lengthwise width of a flattened shape in a cross section perpendicular to a winding direction is no less than twice and no more than four times a lateral width of the flattened shape.

7. The endoscope device according to claim 6, wherein the tight binding thread includes a fiber formed of at least one resin selected from an aramid resin, a polyarylate resin, and a polyester resin.

8. The endoscope device according to claim 6, wherein the tight binding thread is formed by winding a raw material thread whose thickness, which is a lateral width of a flattened shape, is no less than 0.01 mm and no more than 0.3 mm when the raw material thread is sandwiched between surfaces and is pressed with a force of 3.5 N in a straight-line state in which no tensile force is applied.

* * * * *